(12) United States Patent
Radwanski et al.

(10) Patent No.: US 10,039,877 B2
(45) Date of Patent: *Aug. 7, 2018

(54) APHERESIS PLATELETS WITH FIXED RESIDUAL PLASMA VOLUME

(71) Applicant: Fenwal, Inc., Lake Zurich, IL (US)

(72) Inventors: Katherine Radwanski, Des Plaines, IL (US); Kyungyoon Min, Kildeer, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,973

(22) Filed: Aug. 23, 2013

(65) Prior Publication Data

US 2015/0056602 A1    Feb. 26, 2015

(51) Int. Cl.
| | |
|---|---|
| A61J 1/05 | (2006.01) |
| A61K 35/14 | (2015.01) |
| A61K 35/19 | (2015.01) |
| C12N 5/078 | (2010.01) |
| A61M 1/36 | (2006.01) |
| A01N 1/02 | (2006.01) |
| A61M 1/02 | (2006.01) |

(52) U.S. Cl.
CPC ......... *A61M 1/3696* (2014.02); *A01N 1/021* (2013.01); *A01N 1/0226* (2013.01); *A61M 1/0272* (2013.01); *A61M 1/3693* (2013.01); *A61M 2202/0427* (2013.01)

(58) Field of Classification Search
None
See application file for complete search history.

(56) References Cited

U.S. PATENT DOCUMENTS

| | | | | |
|---|---|---|---|---|
| 2002/0032398 | A1* | 3/2002 | Steele | A61M 1/3624 604/6.01 |
| 2006/0161092 | A1* | 7/2006 | Westberg | A61M 1/1037 604/6.01 |
| 2008/0050275 | A1* | 2/2008 | Bischof | A01N 1/02 422/32 |
| 2009/0259162 | A1* | 10/2009 | Ohashi | A61M 1/0209 604/6.01 |
| 2010/0234788 | A1* | 9/2010 | Pages | A61M 1/0209 604/6.04 |
| 2012/0225419 | A1 | 9/2012 | Min et al. | |
| 2013/0280342 | A1* | 10/2013 | Pages | A61M 1/38 424/530 |

FOREIGN PATENT DOCUMENTS

WO    WO 2012/139017    10/2012

OTHER PUBLICATIONS

Extended European Search Report dated Dec. 15, 2014 for European Patent Application No. 13194899.

* cited by examiner

*Primary Examiner* — Chris R Tate
*Assistant Examiner* — Douglas F White
(74) *Attorney, Agent, or Firm* — Cook Alex Ltd.

(57) ABSTRACT

Methods and systems for obtaining platelets are disclosed. Platelets are collected in a pre-determined volume of plasma and a determined amount of a combined storage medium including the pre-determined amount of plasma and a volume of a synthetic additive solution.

15 Claims, 4 Drawing Sheets

APHERESIS PLATELETS WITH FIXED RESIDUAL PLASMA VOLUME

FIELD OF THE DISCLOSURE

The present disclosure is directed to systems and methods for collecting blood platelets. More particularly, the present disclosure is directed to systems and methods for collecting platelets with a fixed volume of residual plasma.

BACKGROUND

Whole blood is made up of various cellular components such as red cells, white cells and platelets suspended in its liquid component, plasma. Whole blood can be separated into its constituent components (cellular or liquid), and the desired separated component can be administered to a patient in need of that particular component. For example, platelets can be removed from the whole blood of a healthy donor, collected, and later administered to a cancer patient whose ability to "make" platelets has been compromised by chemotherapy or radiation treatment.

Commonly, platelets are collected by introducing whole blood into a centrifuge chamber wherein the whole blood is separated into its constituent components, including platelets, based on the size and densities of the different components. This requires that the whole blood be passed through a centrifuge after it is withdrawn from, and before it is returned to, the donor. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted cooperatively on the hardware. The centrifuge assembly spins a disposable centrifuge chamber in the fluid processing assembly during a collection procedure, thereby separating the blood into its constituent components.

Automated blood separation systems are used to collect large numbers of platelets. Automated systems perform the separation steps necessary to separate platelets from whole blood in a sequential process with the donor present. Automated systems draw whole blood from the donor, separate out the desired platelets from the drawn blood, and return the remaining red blood cells and plasma to the donor, all in a sequential flow loop. Large volumes of whole blood can be processed using an automated on-line system. Due to the large processing volumes, large yields of concentrated platelets can be collected. Moreover, since the donor's red blood cells are returned, the donor can donate platelets for on-line processing much more frequently.

In the automated, on-line separation and collection of platelets, sometimes referred to as platelet apheresis, or simply "plateletpheresis", the platelets are separated from whole blood and concentrated in the centrifuge chamber or elsewhere in the fluid processing set (hereinafter "platelet concentrate" or "PC"). Although most of the plasma is removed during apheresis, a volume of plasma still remains in the PC, hereinafter referred to as "residual plasma". (Platelets may also be derived from buffy coats obtained from manually collected units of whole blood. A plurality of buffy coats are typically pooled to provide an amount or dose of platelets suitable for transfusion.) The platelets, whether collected by apheresis or from pooled buffy coats, are typically reconstituted in a liquid storage medium, such as plasma and/or a synthetic storage solution, for storage until needed for transfusion to a patient.

For the stored platelets to be suitable for later administration, they must substantially retain their viability and platelet function. A number of interrelated factors may affect platelet viability and function during storage. Some of these factors include the anticoagulant used for blood collection, the method used to prepare the platelets, the type of storage container used, and the medium in which the platelets are stored.

Currently, platelets may be stored for five or even seven days at 22° C. After seven days, however, platelet function may become impaired. In addition to storage time, other storage conditions have been shown to affect platelet metabolism and function including pH, storage temperature, total platelet count, plasma volume, agitation during storage and platelet concentration.

A variety of assays have been developed which attempt to determine the quality of stored platelets and the in vivo viability of those platelets when transfused to a patient. For instance, the percentage of platelets that respond appropriately to an ADP agonist (the ESC assay) and the percentage of platelets that respond appropriately to hypotonic shock (HSR assay) are two assays which are thought to correlate well with viability of stored platelets. ESC is a photometric assessment of discoid platelet shape change in response to an ADP agonist. VandenBroeke, et al., "Platelet storage solution effects on the accuracy of laboratory tests for platelet function: a multi-laboratory study." Vox Sanguinis (2004) 86, 183-188.

The results of the HSR (Hypotonic Shock Response) assay are often considered to correlate strongly with the in vivo effectiveness of platelets when they are introduced into an individual. This assay measures the ability of platelets to recover a discoid shape after swelling in response to a hypotonic environment. Higher scores on either the HSR or ESC assay appear to correlate with increased viability of the platelets when transfused to patients. The methods and uses of the HSR and ESC assays are described in more detail by Holme et al. Transfusion, January 1998; 38:31-40, which is incorporated by reference herein.

Another assay for measuring platelet viability based on platelet shape is the Morphology Score for the platelets during and after storage. Morphology Scores may be determined by, for example, the Kunicki Method, whereby a selected number of platelets in a sample are examined to determine the shape, e.g., discoid, spherical, dendritic or balloon. The number of each shape is then multiplied by a selected multiplier and the resultant numbers are summed to arrive at a Morphology Score. A score of 250-400 is typically indicative of a viable platelet population.

The presence of the glycoprotein P-selectin on the surface of platelets is also used to characterize the viability of platelets upon transfusion with the presence of P-selectin believed to indicate a loss of viability. As described by Holme et al. Transfusion 1997; 37:12-17 and incorporated herein by reference, platelets undergo a shape change transforming from disc shaped to sphere shaped upon platelet activation. This activation is thought to involve the secretion of β-thromboglobulin from the alpha granules resulting in the appearance of P-selectin on the surface of the platelets. Antibodies directed against P-selectin, such as the monoclonal antibody CD62P, are used to detect the presence of P-selectin on the surface of platelets and have been used as a marker of platelet activation and a decreased viability of the platelets upon transfusion.

A further indicator of platelet viability is pH. Stored platelets will typically produce some lactic acid (as a by-product of anaerobic glycolysis.) The increase in lactic acid gradually acidifies the storage media. This acidification of the media alters platelet physiology and morphology such that when the pH of the media drops below about 6.2 the platelets may be considered nonviable.

Although residual plasma is effective for storage of platelets, it may not be the ideal medium for platelet storage because plasma itself is a valuable blood component that can be removed from the platelets and then used or further processed for use in the treatment of patients with other disorders. Another reason for minimizing the volume of plasma from platelet concentrate is to prevent allergic transfusion reactions (ATR) to plasma. There may be other reasons for removing at least some or even most of the plasma from the platelets. For example, the presence of certain antibodies in plasma has been correlated with the occurrence of TRALI (transfusion-related acute lung injury) in some patients. Consequently, while residual plasma may be present to some degree in platelets obtained in an apheresis procedure, it may be desirable to minimize the volume of plasma and combine the residual plasma with a synthetic additive solution.

Thus, platelets may be resuspended and stored in a combined storage medium that includes a relatively small volume of residual plasma and a volume of the synthetic additive solution (AS). In accordance with certain existing protocols, the combination of plasma and a synthetic AS is provided in a pre-selected ratio of plasma to AS.

One such ratio is 35% plasma:65% AS. More recently, as described in U.S. Patent Publication Nos. US 2009/0191537 and International Patent Application Publication WO 2012/139017, the contents of which is incorporated herein by reference in its entirety, the relative percentage of plasma may be reduced further to below 35%, below 20%, and as low as approximately 10%, resulting in a combined storage medium with a plasma to AS ratio of 20:80 and 10:90, respectively.

The desired ratios are often pre-programmed into the collection apparatus (i.e., apheresis device), and the appropriate volumes of plasma and AS are combined, adjusted and sometimes re-adjusted to arrive at the pre-selected ratio. Where a high yield of platelets is collected, a greater volume of the combined storage medium may be required. This may result in including more than the desired volume of plasma in the combined storage medium.

Thus, it would be desirable to provide a storage environment for the extended storage of platelets that includes a minimal amount of plasma that is not tied to a pre-determined ratio of plasma to AS but rather utilizes a fixed volume of residual plasma that does not require adjusting.

SUMMARY

In one aspect, the present disclosure is directed to a method for obtaining platelets in a combined storage medium. The method includes separating platelets from a biological fluid that includes plasma and platelets; collecting a targeted number of platelets; concentrating the separated platelets; removing plasma from the concentrated platelets until the amount of residual plasma remaining with the concentrated platelets reaches a pre-determined volume; determining a volume of a combined storage medium effective for storing the targeted number of platelets; and combining the platelets in the selected volume of residual plasma with an amount of a synthetic additive solution to arrive at the determined volume of said combined storage medium.

In another aspect, the present disclosure is directed to a system for the collection of platelets. The system includes a reusable hardware apparatus with a separation device and a programmable microprocessor driven controller including instructions for processing a biological fluid. The system also includes a disposable processing circuit associated with the apparatus, wherein the circuit includes a processing chamber for receiving a biological fluid and one or more containers for collecting platelets. The controller is programmed to obtain platelets with a pre-determined volume of plasma remaining with said platelets; determine the volume of combined storage medium required based on a targeted number of platelets; and combine the obtained platelets with a synthetic additive solution to arrive at the determined volume of the combined storage medium that includes residual plasma and synthetic additive solution, based on the number of targeted platelets.

In another aspect, the present disclosure is directed to a platelet product that includes approximately $2.0 \times 10^{11}$-$15.0 \times 10^{11}$ platelets; approximately 100-1,200 ml of a combined storage medium including plasma and a synthetic additive solution wherein no more than approximately 10-50 ml is plasma.

DETAILED DESCRIPTION OF THE EMBODIMENTS

The present disclosure is directed to methods and systems for collecting blood platelets or other blood component in a combined storage medium of residual plasma and a synthetic additive solution (AS). The volume of residual plasma is pre-determined and at least substantially fixed to a specific volume or a volume range regardless of the platelet yield. In accordance with the methods and systems disclosed herein, the volume of the AS, on the other hand, is variable and may be determined and/or adjusted based on the targeted platelet yield to arrive at a volume of the combined storage medium that is effective for the storage of platelets for 5, 7, or even up to 9 days.

Figure 1:
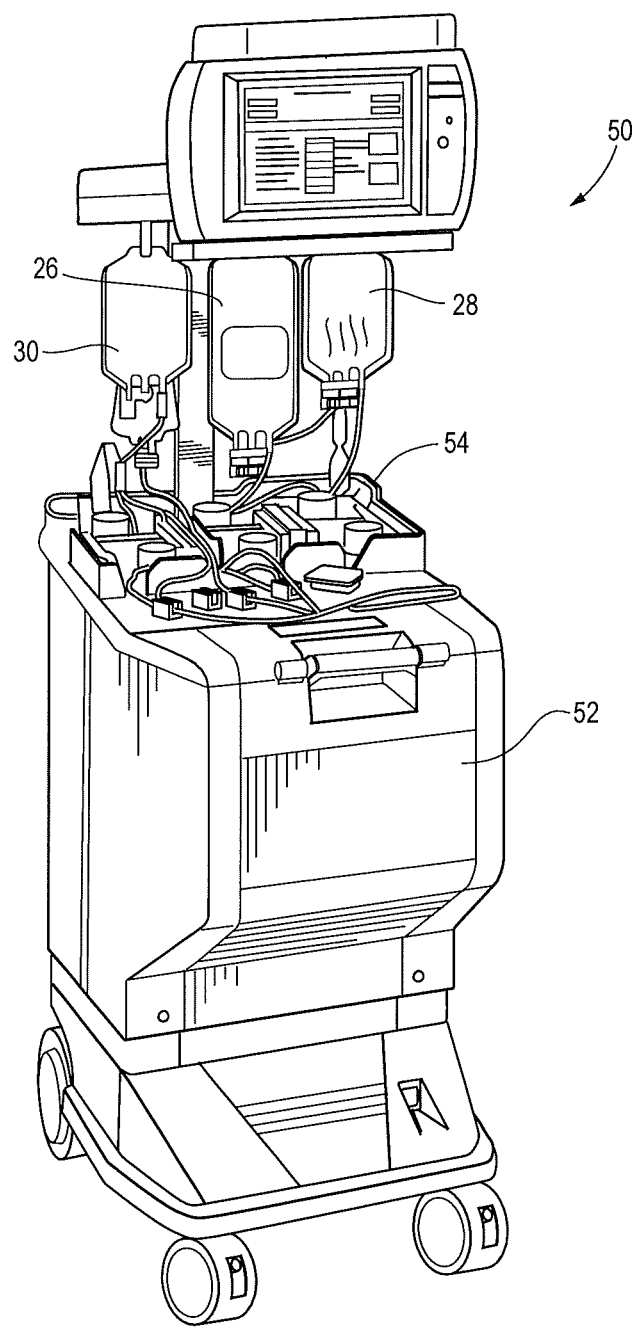
FIG. 1 is a is a perspective view of an automated apheresis device that may be used in the collection and other processing steps of platelets in accordance with the present disclosure.
Figure 2:
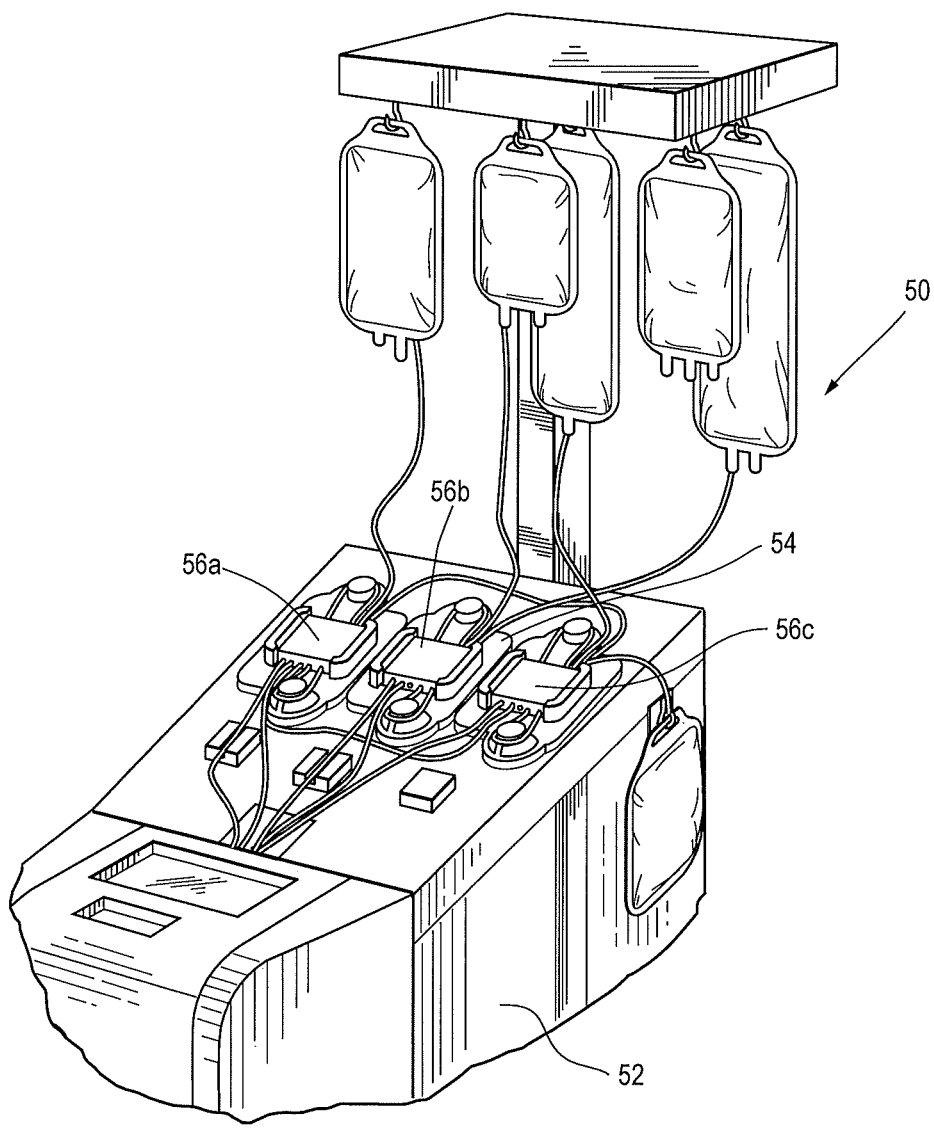
FIG. 2 is an enlarged perspective view of the front panel of the device of FIG. 3 with an exemplary disposable processing set for collecting platelets mounted on the device.

Platelets for storage may be obtained by manual and automated methods. For example, platelets may be collected by known automated apheresis devices, such as the Amicus® Separator, available from Fenwal, Inc., of Lake Zurich, Ill. FIGS. 1 and 2 show a representative separation device useful in the separation and collection of platelets with a minimal amount of residual plasma and the delivery of the additive solution, as described herein. The separator 50 includes a hardware component 52 and a disposable processing kit 54 mounted thereon. In one embodiment, the separation principle used by the separator is based on centrifugation, but an automated separator based on a different separation principle may also be used.

With respect to the device shown in FIGS. 1 and 2, a rotating centrifuge is housed within hardware component 52. Disposable kit 54 includes an access device (e.g., needle) for accessing the vascular system of a donor or other source of biological fluid. Disposable kit 54 also includes the plastic containers for holding fluid and may include a source 26 or 30 of the synthetic additive solution and tubing defining flow paths for movement of the blood, blood components and other fluids through the fluid circuit of kit 54. Disposable processing kit 54 includes one or more cassettes 56 (i.e., cassettes 56a, 56b and 56c, shown in FIG. 2) which interface with the front panel of hardware component 52. Cassettes 56a, 56b and 56c include flow paths and valve stations. A series of pneumatically or electrically operated valves (numbered 1-10 in FIG. 5, for example) under the control of a pre-programmed controller of hardware component 52 selectively allow and restrict flow through the flow paths of the cassette and ultimately through the tubing of disposable kit 54.

Figure 3:
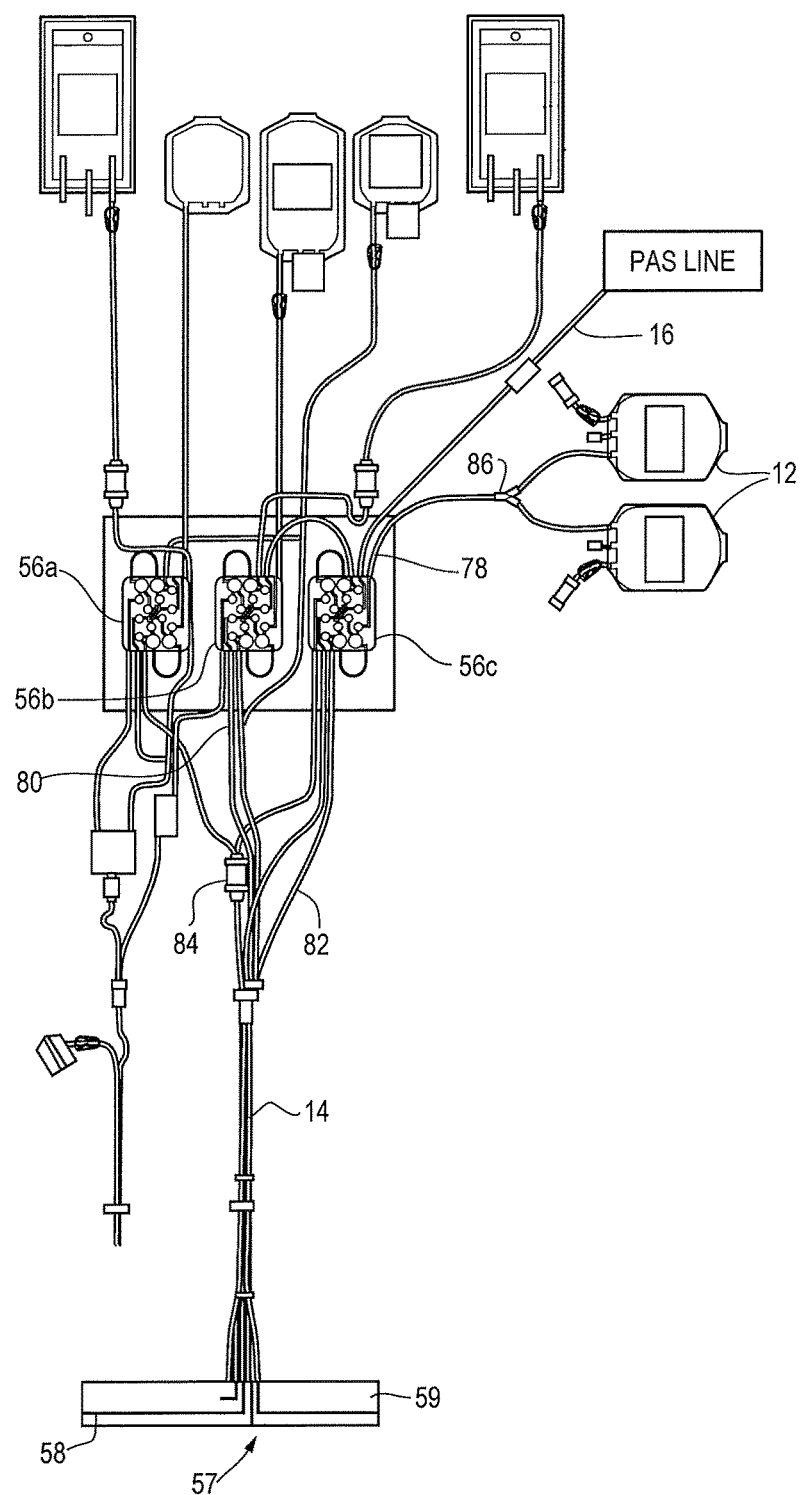
FIG. 3 is a diagram showing the disposable processing set of FIG. 2 with a container of the storage medium disclosed herein.

Disposable kit 54 further includes a processing chamber shown generally at 57 of FIG. 3 (which is mounted on a rotor/spool of the centrifuge). Processing chamber 57 has a sub-chamber 58 wherein blood or blood components are separated under the influence of centrifugal force (i.e., the "separation chamber") and a sub-chamber 59 where blood components from sub-chamber 58 can be further processed, separated and/or collected (i.e., the "concentration" or "collection" chamber). Details of an automated separator suitable for use with the systems and methods described herein are set forth in U.S. Pat. Nos. 5,427,509; 6,312,607; 6,582,349 and U.S. Patent Application Publication 2009/0211987, the entire contents of all of which are incorporated herein by reference.

In one embodiment, an apheresis device may include a programmable controller that is pre-programmed with one or more selectable protocols. A user/operator may select a particular processing protocol to achieve a desired outcome or objective, including, for example, to obtain a platelet product having a pre-determined plasma volume. The pre-programmed selectable protocol(s) may be based on one or more fixed and/or adjustable parameters, including, but not limited to, the volume of fluid being processed, volume of additive solution used or added to the platelets during processing, the desired platelet concentration and/or the desired platelet yield, the desired volume of plasma to be removed or remaining, the processing time/duration of a given procedure and/or desired volume of final platelet product.

During a particular processing procedure, the pre-programmed controller may operate the centrifuge and processing chamber associated therewith to separate blood into its various components, as well as operate one or more pumps to move blood, blood components and/or additive solution through the various openable valves and tubing segments of a processing set 54, such as the one illustrated in FIG. 3. This may include, for example, initiating and causing the centrifugal separation of platelets from whole blood in a separation sub-chamber 58 (or, more specifically, in a separation chamber of a processing chamber), removing plasma from platelets (i.e., pumping the removed plasma to a storage or waste bag) to obtain platelet concentrate, pumping additive solution, such as the synthetic additive solution described below, from a source through selected valves and tubing segments to prime or purge the tubing segments and/or to displace fluid (such as plasma) that may reside or remain in the tubing during or after processing and combining a synthetic additive solution with platelet concentrate in a concentration or collection sub-chamber 59 to reconstitute platelet concentrate therein. The various processing steps performed by the pre-programmed automated apheresis device may occur separately, in series, simultaneously or any combination of these.

In accordance with the present disclosure, an automated apheresis device may be used to perform a procedure that includes, but is not limited to, the steps of separating whole blood in a centrifugal separation chamber to obtain a platelet-rich component, separating plasma from the platelet-rich component in the same or different chamber to obtain a platelet concentrate, removing most of the plasma from the platelet concentrate to arrive at a predetermined volume of residual plasma and reconstituting the platelet concentrate with a synthetic additive to obtain a platelet product in a combined storage medium where the combined storage medium includes the synthetic AS and the fixed residual plasma volume.

Figure 4:
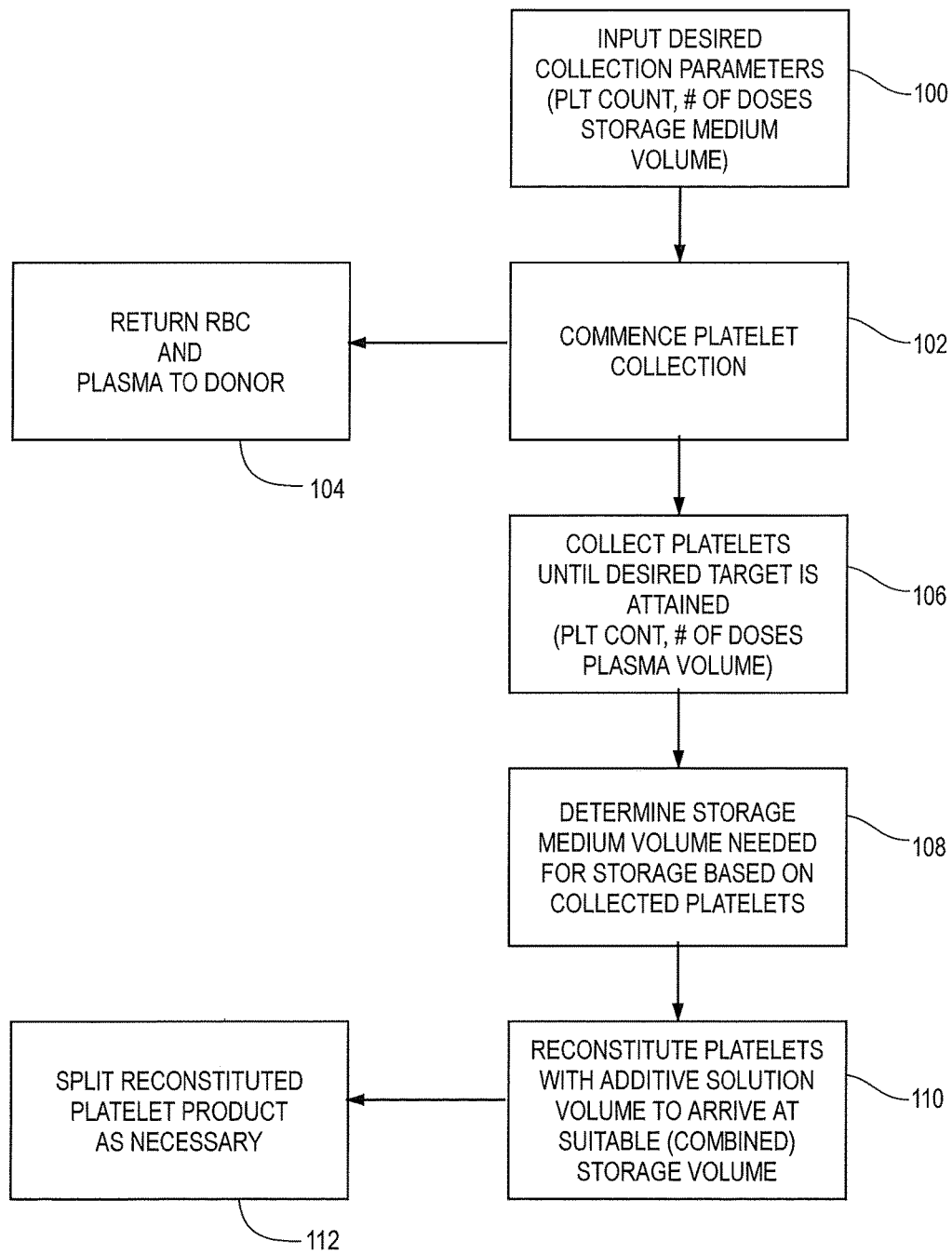
FIG. 4 is a flow diagram of a method for collecting platelets in a combined storage medium in accordance with the present disclosure.

In accordance with the methods of the present disclosure, platelets may be derived from whole blood or other platelet-containing biological fluid. The source of the biological fluid may be a donor who is "connected" to the fluid circuit of the disposable kit 54 or other source of biological fluid. In one embodiment of an automated platelet apheresis procedure, as shown in FIG. 4, the operator may initially select one or more of the targeted number of platelets to be collected or number of units of platelets to be collected, and/or the final storage volume (step 100). In one embodiment, the volume of plasma may be pre-set or pre-determined and serve as a default value. As further shown in FIG. 4, once the initial desired collection parameters have been entered, collection of platelets may commence (102). Platelet collection may begin by first separating platelets from a biological fluid that includes plasma and platelets. In one embodiment, the biological fluid may be whole blood. In another embodiment, the biological fluid may be platelet rich plasma. By way of example, where a dual chambered separator is used, whole blood may be separated into platelet rich plasma and red blood cells in a first stage, i.e., the separation sub-chamber 58 of a dual chambered separator 57. Separated red blood cells and plasma are then returned to the donor (104). The platelet rich plasma may enter a second concentration sub-chamber 59 where platelets are further separated from plasma, concentrated, and collected. Most of the plasma, i.e., platelet-poor-plasma, may likewise be returned to the donor. In one embodiment, the platelets may be hyper-concentrated to provide a concentration of platelets of approximately $5,000\text{-}50,000\times10^3$/microliter. In accordance with the present disclosure, a fixed volume of residual plasma remains with the platelets.

Once the targeted platelet count has been reached, the system will determine the amount of storage medium required for the effective storage of platelets for at least 7 days and/or up to 7 or even 9 days (108). Taking into account the fixed amount of residual plasma, the system will then introduce a sufficient amount of the synthetic additive solution in order to reconstitute the platelet concentrate (110). The fixed amount of residual plasma and the administered or added volume of synthetic additive solution provide the combined storage medium for the platelets.

In one embodiment, the amount of residual plasma remaining with the platelet concentrate (PC) may be a fixed volume, such as approximately 30 ml or no greater than 30 ml, such as, but not limited to, approximately 23-27 ml or, more particularly, 24-26 ml. In another embodiment, the amount of residual plasma may be fixed within a pre-determined range. For example, the amount of residual plasma may be between approximately 10 and 50 ml. In either case, the fixed volume or fixed volume range may be pre-programmed into the controller. The targeted volume may be obtained by the controller monitoring and controlling the flow rates of fluid into and out of collection sub-chamber 59 (see FIG. 3) and, if necessary, removing additional plasma from collection sub-chamber 59 or the fluid circuit 50, as described, for example, in International Patent Application Publication WO 2012/139017, the contents of which is incorporated herein by reference. In accordance with the present disclosure, the amount of residual plasma, whether a fixed volume or a volume within a fixed range, will not vary regardless of the platelet count or the number of platelet doses collected. Thus, for example, where a single dose of platelets, e.g., $3 \times 10^{11}$ platelets, or a double dose of platelets, e.g., $6.0 \times 10^{11}$ platelets, or a triple dose of platelets, e.g. $9.0 \times 10^{11}$ platelets is collected, the volume of residual plasma would be the same, i.e., approximately 30 ml.

The volume of the combined storage medium volume and, therefore, the volume of synthetic additive solution will vary based on the different platelet yields or "doses." Thus, for a single dose, the combined storage volume may be between approximately 100 ml and 300 ml, calling for between approximately 70 ml and 270 ml of synthetic additive solution to be added to the platelets in residual plasma. For a double dose of platelets, the combined storage medium may be between approximately 200 ml and 600 ml, calling for between approximately 170 ml and 570 ml of the synthetic additive solution. For a triple dose of platelets, the combined storage medium may be between approximately 300 ml and 900 ml, calling for between approximately 270 ml and 870 ml of synthetic additive solution. For a quadruple dose of platelets, the combined storage medium may be between approximately 400 ml and 1,200 ml, calling for between approximately 370 ml and 1,170 ml of the synthetic additive solution.

Where multiple containers are provided in the disposable processing set for the collection of platelets, as shown in FIG. 3, the collected platelets will be evenly split among the containers, as will be the fixed volume of residual plasma (step 112 of FIG. 4). Thus, if the amount of residual plasma in a triple dose of platelets is approximately 30 ml, each container will include approximately 10 ml of residual plasma, the platelets and the determined amount of additive solution.

While the volume of residual plasma in the collected platelets may be fixed, the system is capable of determining the amount of synthetic additive solution to be added to the collected platelets to provide a suitable storage environment for the platelets. Thus, a platelet product with a high platelet count such as a double dose or a triple dose of platelets may require a greater amount of synthetic additive solution to arrive at a suitable volume of the combined storage medium.

In an alternative embodiment, the system may also be pre-programmed to deliver a fixed amount of the synthetic additive solution to the collected platelets, based on the total number of platelets collected or the total number of platelet "doses" collected. Thus, for example, for a single dose of platelets, the system may be pre-programmed to automatically add about 220 ml of synthetic additive solution to the platelets, thus providing a combined storage medium of about 250 (about 220 ml of additive solution and about 30 ml of plasma). Where a double dose of platelets are collected, the system may be pre-programmed to automatically deliver a sufficient amount of additive solution to arrive at a preset volume of combined storage medium. For example, where a double dose is collected, the system may deliver 470 ml of the additive solution combined with 30 ml of residual plasma to provide about 500 ml of the combined storage medium. Such double dose platelet product may then be split into separate containers (see FIG. 3) each containing approximately 15 ml of plasma and 235 ml of the additive solution. Where a triple dose of platelets is collected, the system may be pre-programmed to deliver a volume of the synthetic additive solution to arrive at about 750 ml of the combined storage medium. Thus, 720 ml of the synthetic additive solution and 30 ml of plasma would be split into 3 separate containers each containing approximately 10 ml of plasma and 240 ml of the additive solution. Where a quadruple dose of platelets is collected, the system may be pre-programmed to deliver a volume of the synthetic additive solution to arrive at about 1,000 ml of the combined storage medium. Thus, 970 ml of the synthetic additive solution and 30 ml of plasma would be split into 4 separate containers each containing approximately 7.5 ml of plasma and 242.5 ml of the additive solution.

Synthetic additive solutions suitable for use in the methods and systems disclosed herein may be any solution that is capable of preserving platelets for at least 5 days (with or without plasma). For example, one such solution is InterSol®, a commercially available platelet storage medium that is generally described in U.S. Pat. No. 5,908,742, which is incorporated herein in its entirety. InterSol® contains sodium citrate, sodium acetate, sodium phosphate and adjusted to isoosmolarity with sodium chloride. A typical formulation of InterSol® contains 21.5 mM (3.05 g/L) dibasic sodium phosphate anhydrous ($Na_2HPO_4$), 6.7 mM (1.05 g/L) monobasic sodium phosphate ($NaH2PO4.2H_2O$), 10.8 mM (3.18 g/L) sodium citrate $2H_2O$, 32.5 mM (4.42 g/L) sodium acetate $3H_2O$, and 77.3 mM (4.52 g/L) sodium chloride. The InterSol® solution is approximately isoosmolar (about 300 mOsm/L) with platelets and plasma and has a pH of approximately 7.2.

In another embodiment, the synthetic additive solution may include 45-120 mM sodium chloride, 5-15 mM sodium citrate, 20-40 mM sodium acetate, 0.5-12 mM phosphate buffer, 0.05-3 mM magnesium ion, and 0.5-20 mM glucose, with the initial pH of the complete storage media ranging from 6.8-7.3. Optionally, 0.05-3 mM calcium chloride and/or 0.05-10 mM potassium chloride may also be present in synthetic platelet storage solution. More specifically, the additive solution may include about 70 mM sodium chloride; about 10 mM sodium citrate; about 30 mM sodium acetate; about 10 mM sodium phosphate; about 1.5 mM magnesium chloride; about 5 mM potassium chloride; and about 17 mM glucose. Other additive solutions, including the solutions described in U.S. Patent Publication Nos. US 2009/0191537 and International Patent Application Publication WO 2012/139017, both of which are incorporated herein by reference, may also be used in accordance with the methods and systems described herein. In other words, platelets collected with a fixed residual amount of plasma may be reconstituted with determined amounts of any one of the solutions described above or other suitable solutions to provide a combined storage medium for the platelets.

STUDY

Plateletphereis collections were performed with the Amicus® Separator in healthy donors using a double dose platelet yield target of $7.0 \times 10^{11}$ in storage fluid volumes of 500 or 600 ml (containing approximately 30 ml of plasma and 470 or 570 ml of PAS, respectively). Platelet products were split into two units, each containing approximately 15 ml of plasma and 235 or 285 ml of PAS. The resulting platelet products were stored for 7 days with no pH failures (<6.2) observed and acceptable platelet morphology and functionality maintained. Plasma in the combined storage medium was calculated from total protein concentration in the platelet products supernatant divided by total protein concentration in the concurrent plasma.

Tables 1 and 2 set forth the fluid volumes and platelet yields for the 500 ml and 600 ml combined storage volume examples. Table 3 sets forth the composition of the synthetic additive solution. Tables 4 and 5 set forth the platelet viability characteristics of platelets stored in accordance with the storage parameters, solutions, volumes and yields described above.

TABLE 1

| 500 ml Target | n | Mean (SD) |
| --- | --- | --- |
| Storage Fluid - Volume (ml) | 20 | 501 (5) |
| Plasma in Storage - Fluid (ml) | 20 | 25 (2) |
| Plasma in Storage - Fluid (%) | 20 | 5 (1) |
| Platelet Yield - ($\times 10^{11}$) | 20 | 7.0 (1.1) |

TABLE 2

| 600 ml Target | n | Mean (SD) |
| --- | --- | --- |
| Storage Fluid - Volume (ml) | 20 | 611 (6) |
| Plasma in Storage - Fluid (ml) | 20 | 26 (4) |
| Plasma in Storage - Fluid (%) | 20 | 4 (1) |
| Platelet Yield - ($\times 10^{11}$) | 20 | 7.0 (0.7) |

TABLE 3

| Composition (g/L) | PAS |
| --- | --- |
| $Na_3Citrate \cdot 2H_2O$ | 2.91 |
| $Na\ Acetate \cdot 3H_2O$ | 4.04 |
| $NaH_2PO_4 \cdot 2H_2O$ | 0.35 |
| $NaH_2PO_4$ | 1.01 |
| NaCl | 4.15 |
| KCl | 0.37 |
| $MgCl_2$ | 0.30 |
| Glucose | 3.30 |
| Bicarbonate | 1.66 |

TABLE 4

| Platelet Parameters - 500 ml Target | | | |
| --- | --- | --- | --- |
| Mean (SD) | n | Day 1 | Day 7 |
| Plt Conc ($\times 10^3$/uL) | 20 | 1369 (205) | 1414 (222) |
| pH (37 C.) | 20 | 7.27 (0.12) | 7.28 (0.16) |
| HSR (%) | 20 | 63 (16) | 54 (14) |
| ESC (%) | 20 | 22 (6) | 18 (6) |
| CD62p (%) | 20 | 58 (16) | 45 (11) |
| Morphology (0-400) | 20 | 339 (16) | 294 (22) |

TABLE 5

| Platelet Parameters - 600 ml Target | | | |
| --- | --- | --- | --- |
| Mean (SD) | n | Day 1 | Day 7 |
| Plt Conc ($\times 10^3$/uL) | 20 | 1160 (122) | 1214 (125) |
| pH (37 C.) | 20 | 7.24 (0.11) | 7.28 (0.15) |
| HSR (%) | 20 | 76 (21) | 57 (10) |
| ESC (%) | 20 | 23 (7) | 16 (5) |
| CD62p (%) | 20 | 49 (15) | 37 (10) |
| Morphology (0-400) | 20 | 348 (12) | 312 (23) |

EXAMPLES

Without limiting any of the foregoing, the subject matter described herein may be found in one or more methods, systems and/or products. For example, in a first aspect of the present subject matter a method for obtaining platelets in a combined storage medium is set forth. The method includes separating platelets from a biological fluid that includes plasma and platelets; collecting a targeted number of platelets; concentrating separated platelets; removing plasma from the concentrated platelets until the amount of residual plasma remaining with the concentrated platelets reaches a predetermined volume; determining a volume of a combined storage medium suitable for storing the number of platelets targeted; and combining the platelets and the pre-determined volume of residual plasma with that amount of a synthetic additive solution to arrive at the determined volume of the combined storage medium.

A second aspect of the present subject matter includes the above-described method wherein the volume of the residual plasma remaining with the concentrated platelets is approximately 10-50 ml.

A third aspect of the present subject matter includes the method in accordance with any one of the first or second aspects wherein the residual volume of plasma remaining with the concentrated platelets is approximately 30 ml.

A fourth aspect of the present subject matter includes the method in accordance with any one of the first through third aspects described above wherein the number of platelets is about $2.0 \times 10^{11}$ to about $15 \times 10^{11}$.

A fifth aspect of the present subject matter includes the method in accordance with any one of the first through fourth aspects described above wherein the volume of the combined storage medium is about 100-1,200 ml.

A sixth aspect of the present subject matter includes the method in accordance with any one of the first through fifth aspects described above wherein the volume of the combined storage medium is about 250-750 ml.

A seventh aspect of the present subject matter includes the method in accordance with any one of the first through sixth aspects described above wherein the ratio of residual plasma to the synthetic additive solution is between about 1:99 and 50:50.

An eighth aspect of the present subject matter includes the method in accordance with any one of the first through seventh aspects described above wherein the ratio of residual plasma to additive solution is between about 35:65 and 5:95.

A ninth aspect of the present subject matter includes a method in accordance with any one of the first through eighth aspects described above further including collecting platelets and the combined storage medium in one or more collection containers.

A tenth aspect of the present subject matter includes a method in accordance with any one of the first through ninth aspects described above including separating and concentrating the platelets in one or more chambers of a processing apparatus.

An eleventh aspect of the present subject matter includes the method in accordance with the tenth aspect described above further including subjecting the processing apparatus to a centrifugal field sufficient to separate and concentrate the platelets.

A twelfth aspect of the present subject matter includes the method in accordance with any one of the first through eleventh aspects described above including concentrating the platelets to approximately $5{,}000\text{-}50{,}000 \times 10^3$ platelets/microliter.

A thirteenth aspect of the present subject matter includes the method in accordance with any one of the first through twelfth aspects described above including adjusting the amount of the synthetic additive solution to arrive at the volume of the combined storage medium.

A fourteenth aspect of the present subject matter includes the method in accordance with any one of the first through thirteenth aspects described above wherein the biological fluid is whole blood.

In a fifteenth aspect of the present subject matter, a system for the collection of platelets is set forth. The system includes a reusable hardware apparatus that includes a separation device and a programmable microprocessor driven controller including instructions for processing a biological fluid; a disposable processing circuit associated with the apparatus, the circuit including a processing chamber for receiving a biological fluid and one or more containers for collecting platelets. The controller is programmed to obtain platelets with a pre-determined volume of plasma remaining with the platelets; determine an effective volume of a combined storage medium based on a targeted number of platelets; and combine the obtained platelets with a synthetic additive solution to arrive at the effective volume of the combined storage medium of residual plasma and synthetic additive solution based on the targeted number of platelets.

A sixteenth aspect of the present subject matter includes the system in accordance with the fifteenth aspect described above wherein the separation device includes a rotatable element.

The seventeenth aspect of the present subject matter includes the system in accordance with any one of the fifteenth or sixteenth aspects described above wherein the rotatable element generates a centrifugal field sufficient to separate platelets from other components of a biological fluid.

An eighteenth aspect of the present subject matter includes the system in accordance with the seventeenth aspect described above further including a source of a synthetic additive solution.

A nineteenth aspect of the present subject matter includes the system in accordance with any one of the fifteenth through eighteenth aspects described above wherein the controller is programmed to deliver a selected volume of the synthetic additive solution to concentrated platelets in the residual amount of plasma.

A twentieth aspect of the present subject matter includes the system in accordance with any one of the fifteenth through nineteenth aspects described above wherein the processing chamber is mountable on a rotatable member and the processing chamber separation comprises a separation chamber and a collection chamber.

In a twenty-first aspect of the present subject matter a platelet product including approximately $2.0 \times 10^{11}\text{-}15.0 \times 10^{11}$ platelets and approximately 200-1,000 ml of a combined storage medium including residual plasma and a synthetic storage medium wherein no more than approximately 10-50 ml is plasma.

A twenty-second aspect of the present subject matter includes the product of the twenty-first aspect described above wherein the volume of plasma is no greater than about 30 ml.

A twenty-third aspect of the present subject matter includes the platelet product in accordance with any one of the twenty-first or twenty-second aspects described above wherein the synthetic additive solution includes sodium citrate, sodium acetate and sodium chloride.

A twenty-fourth aspect of the present subject matter includes the platelet product in accordance with any one of the twenty-first through twenty-third aspects described above wherein the synthetic additive solution further includes sodium phosphate.

A twenty-fifth aspect of the present subject matter includes the platelet product in accordance with any one of the twenty-first through twenty-fourth aspects described above wherein the synthetic additive solution further includes one or more of magnesium, calcium, adenine, and bicarbonate.

It should be understood that various changes and modifications to the presently preferred embodiments described herein will be apparent to those skilled in the art. Such changes and modification can be made without departing from the spirit and scope of the invention disclosed herein.

The invention claimed is:

1. A method for obtaining platelets in a combined storage medium comprising:
   a) separating platelets from a biological fluid that includes plasma and platelets;
   b) collecting a targeted number of the separated platelets;
   c) concentrating said collected platelets to approximately $5{,}000\text{-}50{,}000 \times 10^3$ platelets/microliter, wherein the concentrated platelets contain an amount of residual plasma, said amount comprising a predetermined default volume or a volume within a default volume range, wherein said default volume or default volume range is a fixed volume or a fixed volume range regardless of platelet count or number of platelet doses collected; and
   d) combining said concentrated platelets and said residual plasma from step c) with a synthetic additive solution to arrive at a determined final combined storage medium volume, wherein said final combined storage medium volume comprises said fixed volume or said fixed volume range and a volume of said synthetic storage medium sufficient to arrive at said final combined storage medium volume.

2. The method of claim 1 wherein said pre-determined volume range of residual plasma remaining with said concentrated platelets is approximately 10-50 ml.

3. The method of claim 1 wherein said pre-determined volume of residual plasma remaining with said concentrated platelets is approximately 30 ml.

4. The method of claim 1 wherein said number of platelets is about $2.0 \times 10^{11}$ to about $15.0 \times 10^{11}$.

5. The method of claim 1 further comprising collecting said platelets and said combined storage medium in one or more collection containers.

6. The method of claim 1 wherein said biological fluid comprises whole blood.

7. The method of claim 1 wherein said pre-determined volume of residual plasma is independent of the number of platelet doses.

8. The method of claim 1 comprising pre-selecting the amount of plasma prior to said separating.

9. The method of claim 1 comprising adjusting the volume of plasma until the amount of residual plasma remaining with the concentrated platelets reaches said pre-determined default volume or said volume within the default volume range.

10. The method of claim 1 wherein the volume of the combined storage medium is about 100-1,200 ml.

11. The method of claim 10 wherein the volume of the combined storage medium is about 250-750 ml.

12. The method of claim 1 wherein the steps a-c comprise separating and concentrating said platelets in one or more chambers of a processing apparatus.

13. The method of claim 12 comprising subjecting said processing apparatus to a centrifugal field sufficient to separate and concentrate said platelets.

14. The method of claim 1 wherein said volume of residual plasma volume is divided among a plurality of platelet doses.

15. The method of claim 14 wherein said volume of residual plasma is divided among a plurality of platelet doses in equal amounts.

* * * * *